United States Patent
Wang et al.

(10) Patent No.: US 6,815,609 B1
(45) Date of Patent: Nov. 9, 2004

(54) NANOMAGNETIC COMPOSITION

(75) Inventors: Xingwu Wang, Wellsville, NY (US); Howard J. Greenwald, Rochester, NY (US); Ronald E. Miller, Kintnersville, PA (US)

(73) Assignee: Nanoset, LLC, West Henrietta, NY (US)

( * ) Notice: Subject to any disclaimer, the term of this patent is extended or adjusted under 35 U.S.C. 154(b) by 23 days.

(21) Appl. No.: 10/409,505

(22) Filed: Apr. 8, 2003

Related U.S. Application Data

(63) Continuation-in-part of application No. 10/324,773, filed on Dec. 18, 2002.

(51) Int. Cl.$^7$ ................................................ H05K 9/00
(52) U.S. Cl. .................. 174/35 MS; 428/323; 428/340
(58) Field of Search .......................... 174/35 MS, 35 R; 361/816, 818, 800; 428/323, 340

(56) References Cited

U.S. PATENT DOCUMENTS

| | | | | | |
|---|---|---|---|---|---|
| 5,864,088 A | * | 1/1999 | Sato et al. | ............. | 174/35 MS |
| 6,048,601 A | * | 4/2000 | Yahagi et al. | ............... | 428/147 |
| 6,713,671 B1 | * | 3/2004 | Wang et al. | ........... | 174/35 MS |

* cited by examiner

Primary Examiner—Hung V. Ngo
(74) Attorney, Agent, or Firm—Howard J. Greenwald

(57) ABSTRACT

A magnetically shielded substrate assembly includes a substrate and, disposed over the substrate, a magnetic shield with a magnetic shielding factor of at least about 0.5. The magnetic shield has a film of nanomagnetic material containing at least about 40 weight percent of nomagnetic material with a mass density of at least about 0.01 grams per cubic centimeter, a saturization magnetization of from about 1 to about 36,000 Gauss, a coercive force of from about 0.01 to about 5,000 Oersteds, a relative magnetic permeability of from about 1 to about 500,000, and an average particle size of less than about 100 nanometers. This film of nanomagnetic material has a squareness of from about 0.5 to about 1.0.

18 Claims, 3 Drawing Sheets

NANOMAGNETIC COMPOSITION

CROSS-REFERENCE TO RELATED PATENT APPLICATION

This patent application is a continuation-in-part of applicants' copending patent application U.S. Ser. No. 10/324,773, filed on Dec. 18, 2002.

FIELD OF THE INVENTION

A magnetically shielded substrate with a layer of magnetic shielding material that has a squareness of from about 0.5 to about 1.0.

BACKGROUND OF THE INVENTION

U.S. Pat. No. 6,506,972 discloses and claims a magnetically shielded conductor assembly containing a conductor disposed within an insulating matrix, and a layer composed of nanomagentic material disposed around the first conductor. The conductor has a resistivity at 20 degrees Centigrade of from about 1 to about 100 microohm-centimeters. The insulating matrix is comprised of nano-sized particles having a maximum dimension of from about 10 to about 100 nanometers. The insulating matrix has a resistivity of from about 1,000,000,000 to about 10,000,000,000,000 ohm-centimeter. The nanomagnetic material has an average particle size of less than about 100 nanometers. The layer of nanomagnetic material has a saturation magnetization of from about 200 to about 26,000 Gauss and a thickness of less than about 2 microns. The magnetically shielded conductor assembly is preferably flexible, having a bend radius of less than 2 centimeters.

The entire disclosure of U.S. Pat. No. 6,506,972 is hereby incorporated by reference into this specification. It is an object of this invention to provide a magnetic shield that is more effective than the magnetic shield disclosed in such United States patent.

SUMMARY OF THE INVENTION

In accordance with this invention, there is provided a magnetically shielded substrate assembly comprised of a substrate and, disposed over such substrate, a magnetic shield. The magnetic shield, when exposed to a magnetic field with an intensity of at least 0.5 Teslas, has a magnetic shielding factor of at least about 0.5. The magnetic shield is comprised of a film of nanomagnetic material comprising at least about 40 weight percent of nanomagnetic material with a mass density of at least about 0.01 grams per cubic centimeter, a saturization magnetization of from about 1 to about 36,000 Gauss, a coercive force of from about 0.01 to about 5,000 Oersteds, a relative magnetic permeability of from about 1 to about 500,000, and an average particle size of less than about 100 nanometers. The film of nanomagnetic material has a squareness of from about 0.5 to about 1.0.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
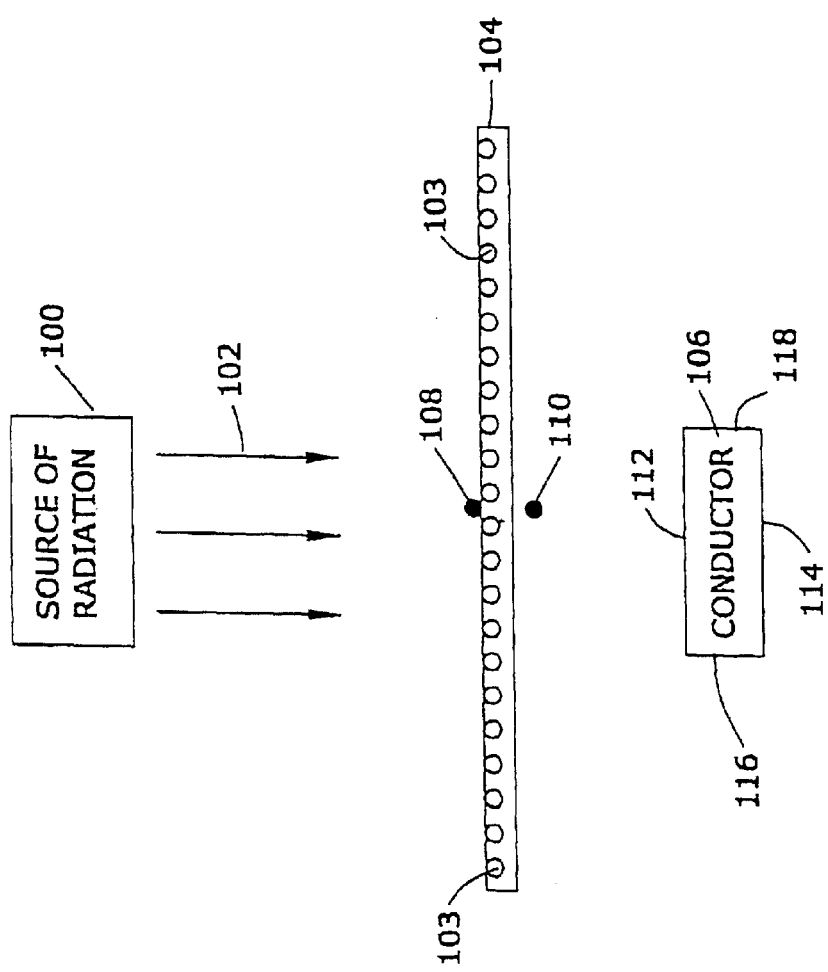
FIG. 1 is a schematic illustration of one preferred process of the invention.

FIG. 1 is a schematic illustration of one preferred process of the invention. Referring to FIG. 1, and to the preferred embodiment depicted therein, it will be seen that there is provided a magnetically shielded conductor assembly comprised of a conductor and a film of nanomagnetic material disposed above said conductor. In this embodiment, the conductor preferably has a resistivity at 20 degrees Centigrade of from about 1 to about 2,000 micro ohm-centimeters and is comprised of a first surface exposed to electromagnetic radiation. In this embodiment, the film of nanomagnetic material preferably has a thickness of from about 100 nanometers to about 10 micrometers and a mass density of at least about 1 gram per cubic centimeter, wherein the film of nanomagnetic material is disposed above at least about 50 percent of said first surface exposed to electromagnetic radiation, and the film of nanomagnetic material has a saturation magnetization of from about 1 to about 36,000 Gauss, a coercive force of from about 0.01 to about 5,000 Oersteds, a relative magnetic permeability of from about 1 to about 500,000, and a magnetic shielding factor of at least about 0.5. In this embodiment, the nanomagnetic material has an average particle size of less than about 100 nanometers.

Referring to FIG. 1, and in the schematic diagram depicted therein, a source of electromagnetic radiation 100 emits radiation 102 in the direction of film 104. Film 104 is disposed above conductor 106, i.e., it is disposed between conductor 106 of the electromagnetic radiation 102.

The film 104 is adapted to reduce the magnetic field strength at point 108 (which is disposed less than 1 centimeter above film 104) by at least about 50 percent. Thus, if one were to measure the magnetic field strength at point 108, and thereafter measure the magnetic field strength at point 110 (which is disposed less than 1 centimeter below film 104), the latter magnetic field strength would be no more than about 50 percent of the former magnetic field strength. Put another way, the film 104 has a magnetic shielding factor of at least about 0.5.

In one embodiment, the film 104 has a magnetic shielding factor of at least about 0.9, i.e., the magnetic field strength at point 110 is no greater than about 10 percent of the magnetic field strength at point 108. Thus, e.g., the static magnetic field strength at point 108 can be, e.g., one Tesla, whereas the static magnetic field strength at point 110 can be, e.g., 0.1 Tesla. Furthermore, the time-varying magnetic field strength of a 100 milliTesla would be reduced to about 10 milliTesla of the time-varying field.

Referring again to FIG. 1, the nanomagnetic material 103 in film 104 has a saturation magnetization of form about 1 to about 36,000 Gauss. This property has been discussed in U.S. Pat. No. 6,506,972, the entire disclosure of which is hereby incorporated by reference into this specification. In one embodiment, the nanomagnetic material 103 has a saturation magnetization of from about 200 to about 26,000 Gauss.

The nanomagnetic material 103 in film 104 also has a coercive force of from about 0.01 to about 5,000 Oersteds. The term coercive force refers to the magnetic field, H, which must be applied to a magnetic material in a symmetrical, cyclicly magnetized fashion, to make the magnetic induction, B, vanish; this term often is referred to as magnetic coercive force. Reference may be had, e.g., to U.S. Pat. Nos. 4,061,824, 6,257,512, 5,967,223, 4,939,610, 4,741,953, and the like. The entire disclosure of each of these United States patents is hereby incorporated by reference into this specification.

In one embodiment, the nanomagnetic material 103 has a coercive force of from about 0.01 to about 3,000 Oersteds. In yet another embodiment, the nanomagnetic material 103 has a coercive force of from about 0.1 to about 10.

Referring again to FIG. 1, the nanomagnetic material 103 in film 104 preferably has a relative magnetic permeability of from about 1 to about 500,000; in one embodiment, such material 103 has a relative magnetic permeability of from about 1.5 to about 260,000. As used in this specification, the term relative magnetic permeability is equal to B/H, and is also equal to the slope of a section of the magnetization curve of the film. Reference may be had, e.g., to page 4–28 of E. U. Condon et al.'s "Handbook of Physics" (McGraw-Hill Book Company, Inc., New York, 1958).

Reference also may be had to page 1399 of Sybil P. Parker's "McGraw-Hill Dictionrary of Scientific and Technical Terms," Fourth Edition (McGraw Hill Book Company, New York, 1989). As is disclosed on this page 1399, permeability is " . . . a factor, characteristic of a material, that is proportional to the magnetic induction produced in a material divided by the magnetic field strength; it is a tensor when these quantities are not parallel."

Reference also may be had, e.g., to U.S. Pat. Nos. 6,181,232, 5,581,224, 5,506,559, 4,246,586, 6,390,443, and the like. The entire disclosure of each of these United States patents is hereby incorporated by reference into this specification.

In one embodiment, the nanomagnetic material 103 in film 104 has a relative magnetic permeability of from about 1.5 to about 2,000.

Referring again to FIG. 1, the nanomagnetic material 103 in film 104 preferably has a mass density of at least about 0.001 grams per cubic centimeter; in one embodiment, such mass density is at least about 1 gram per cubic centimeter. As used in this specification, the term mass density refers to the mass of a give substance per unit volume. See, e.g., page 510 of the aforementioned "McGraw-Hill Dictionary of Scientific and Technical Terms." In one embodiment, the film 104 has a mass density of at least about 3 grams per cubic centimeter. In another embodiment, the nanomagnetic material 103 has a mass density of at least about 4 grams per cubic centimeter.

In the embodiment depicted in FIG. 1, the film 104 is disposed above 100 percent of the surfaces 112, 114, 116, and 118 of the conductor 106. In another embodiment, not shown, the nanomagnetic film is disposed around a conductor.

The conductor 106 may comprise or consist of any conductive material(s) that have a resistivity at 20 degrees Centigrade of from about 1 to about 100 microohm-centimeters. Thus, e.g., the conductive material(s) may be silver, copper, aluminum, alloys thereof, mixtures thereof, and the like.

In one embodiment, the conductor 106 consists essentially of such conductive material. Thus, e.g., it is preferred not to use, e.g., copper wire coated with enamel. The use of such typical enamel coating on the conductor does not work well in the instant invention.

Figure 1A:
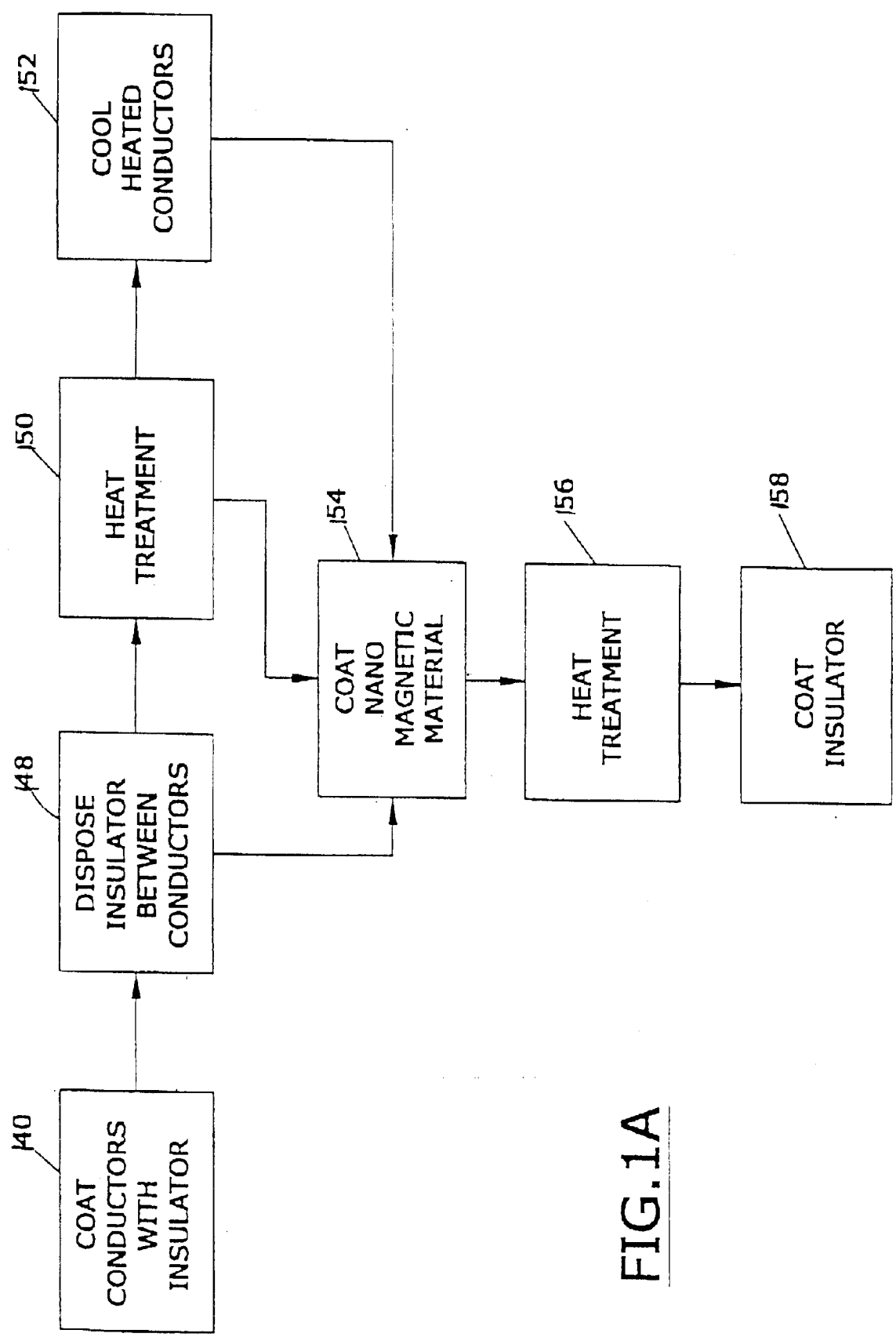
FIG. 1A is a block diagram of one preferred process of the invention.

FIG. 1A is a flow diagram illustrating one preferred process of the invention.

In the first step of one embodiment of the process of FIG. 1, step 140, two conductive wires (not shown) are coated with electrically insulative material. Suitable insulative materials include nano-sized silicon dioxide, aluminum oxide, cerium oxide, yttrium-stabilized zirconia, silicon carbide, silicon nitride, aluminum nitride, and the like. In general, these nano-sized particles will have a particle size distribution such that at least about 90 weight percent of the particles have a maximum dimension in the range of from about 10 to about 100 nanometers.

The coated conductors (not shown) may be prepared by conventional means such as, e.g., the process described in U.S. Pat. No. 5,540,959, the entire disclosure of which is hereby incorporated by reference into this specification. This patent describes and claims a process for preparing a coated substrate, comprising the steps of: (a) creating mist particles from a liquid, wherein: 1. said liquid is selected from the group consisting of a solution, a slurry, and mixtures thereof, 2. said liquid is comprised of solvent and from 0.1 to 75 grams of solid material per liter of solvent, 3. at least 95 volume percent of said mist particles have a maximum dimension less than 100 microns, and 4. said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist particles to a temperature of at least about 100 degrees centigrade, thereby producing a heated vapor; (d) depositing said heated vapor onto a substrate, thereby producing a coated substrate; and (e) subjecting said coated substrate to a temperature of from about 450 to about 1,400 degrees centigrade for at least about 10 minutes.

By way of further illustration, one may coat conductors by means of the processes disclosed in a text by D. Satas on "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like. One may also use one or more of the processes disclosed in this book for preparing other coated members.

By way of yet further illustration, one may coat the conductors with the sputtering process described elsewhere in this specification.

Referring again to FIG. 1A, in step 148 of the process depicted one may dispose insulating material between the conductors. Thus, e.g., one may simultaneously coat the two conductors with the insulating material so that such insulators both coat the conductors and fill in the distance between them with insulation.

The insulating material that is disposed between conductors generally has a resistivity of from about 1,000,000,000 to about 10,000,000,000,000 ohm-centimeters.

After the insulating material has been deposited, and in one embodiment, the coated conductor assembly is preferably heat treated in step 150. This heat treatment often is used in conjunction with coating processes in which the heat is required to bond the insulative material to the conductors.

The heat-treatment step may be conducted after the deposition of the insulating material, or it may be conducted simultaneously therewith. In either event, and when it is used, it is preferred to heat the coated conductors to a temperature of from about 200 to about 600 degrees Centigrade for from about 1 minute to about 10 minutes.

Referring again to FIG. 1A, and in step 152 of the process, after the coated conductors have been subjected to heat treatment step 150, they are allowed to cool to a temperature of from about 30 to about 100 degrees Centigrade over a period of time of from about 3 to about 15 minutes.

One need not invariably heat treat and/or cool. Thus, referring to FIG. 1A, one may immediately coat nanomagnetic particles onto to the coated conductors in step 154 either after step 148 and/or after step 150 and/or after step 152.

In step 154, nanomagnetic materials are coated onto the previously coated conductors.

In general, and as is known to those skilled in the art, nanomagnetic material is magnetic material which has an average particle size less than 100 nanometers and, preferably, in the range of from about 2 to 50 nanometers. Reference may be had, e.g., to U.S. Pat. No. 5,889,091 (rotationally free nanomagnetic material), U.S. Pat. Nos. 5,714,136, 5,667,924, and the like. The entire disclosure of each of these United States patents is hereby incorporated by reference into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, chromium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. De Marco, X. W. Wang, et al. on "Mossbauer and magnetization studies of nickel ferrites" published in the Journal of Applied Physics 73(10), May 15, 1993, at pages 6287–6289.

In general, the thickness of the layer of nanomagnetic material deposited onto the coated conductors is less than about 5 microns and generally from about 0.1 to about 3 microns.

After the nanomagnetic material is coated in step 154, the coated assembly may be optionally heat-treated in step 156. In this optional step 156, it is preferred to subject the coated conductors to a temperature of from about 200 to about 600 degrees Centigrade for from about 1 to about 10 minutes.

In one embodiment, one or more additional insulating layers are coated onto the coated substrate(s) by one or more of the processes disclosed hereinabove. This is conducted in optional step 158 (see FIG. 1A).

Referring again to FIG. 1, and in the preferred embodiment depicted therein, the nanomagnetic particles 103 are present in a density sufficient so as to provide shielding from magnetic flux lines 102. Without wishing to be bound to any particular theory, applicant believes that the nanomagnetic particles 103 trap and pin the magnetic lines of flux 102.

In order to function optimally, the nanomagnctic particles 103 preferably have a specified magnetization. As is known to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

Referring again to FIG. 1, the layer 104 of nanomagnetic particles 103 preferably has a saturation magnetization, at 25 degrees Centigrade, of from about 1 to about 36,000 Gauss, or higher. In one embodiment, the saturation magnetization at room temperature of the nanomagentic particles is from about 500 to about 10,000 Gauss. For a discussion of the saturation magnetization of various materials, reference may be had, e.g., to U.S. Pat. Nos. 4,705,613, 4,631,613, 5,543,070, 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagnetic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film has a saturation magnetization of 24,000 Gauss.

By the appropriate selection of nanomagnetic particles, and the thickness of the films deposited, one may obtain saturation magnetizations of as high as at least about 36,000.

In the preferred embodiment depicted in FIG. 1, the nanomagnetic particles 103 are disposed within an insulating matrix so that any heat produced by such particles will be slowly dispersed within such matrix. Such matrix, as indicated hereinabove, may be made from ceria, calcium oxide, silica, alumina. In general, the insulating material preferably has a thermal conductivity of less than about 20 (calories-centimeters/square centimeters–degree second)× 10,000. See, e.g., page E-6 of the $63^{rd}$ Edition of the "Handbook of Chemistry and Physics" (CRC Press, Inc., Boca Raton, Fla., 1982).

The nanomagnetic materials 103 typically comprise one or more of aluminum iron, cobalt, nickel, gadolinium, and samarium atoms. Thus, e.g., typical nanomagnetic materials include alloys of iron and nickel (permalloy), iron and aluminum, cobalt, niobium, and zirconium (CNZ), iron, boron, and nitrogen, cobalt, iron, boron, and silica, iron, cobalt, boron, and fluoride, and the like. These and other materials are descried in a book by J. Douglas Adam et al. entitled "Handbook of Thin Film Devices" (Academic Press, San Diego, Calif. 2000). Chapter 5 of this book beginning at page 185, describes "magnetic films for planar inductive components and devices;" and Tables 5.1 and 5.2 in this chapter describe many magnetic materials.

Referring again to FIG. 1, the nanomagnetic material 103 in film 104 preferably has a mass density of at least about 0.001 grams per cubic centimeter; in one embodiment, such mass density is at least about 1 gram per cubic centimeter. As used in this specification, the term mass density refers to the mass of a give substance per unit volume. See, e.g., page 510 of the aforementioned "McGraw-Hill Dictionary of Scientific and Technical Terms." In one embodiment, the film 104 has a mass density of at least about 3 grams per cubic centimeter. In another embodiment, the nanomagnetic material 103 has a mass density of at least about 4 grams per cubic centimeter.

A Process for Preparation of an Iron-Containing thin Film

In one preferred embodiment of the invention, a sputtering technique is used to prepare an AlFe thin film as well as comparable thin films containing other atomic moieties, such as, e.g., elemental nitrogen, and elemental oxygen. Conventional sputtering techniques may be used to prepare such films by sputtering. See, for example, R. Herrmann and G. Brauer, "D.C.- and R.F. Magnetron Sputtering," in the "Handbook of Optical Properties: Volume I—Thin Films for Optical Coatings," edited by R. E. Hummel and K. H. Guenther (CRC Press, Boca Raton, Fla., 1955). Reference also may be had, e.g., to M. Allendorf, "Report of Coatings on Glass Technology Roadmap Workshop," Jan. 18–19, 2000, Livermore, Calif.; and also to U.S. Pat. No. 6,342,134, "Method for producing piezoelectric films with rotating magnetron sputtering system." The entire disclosure of each of these prior art documents is hereby incorporated by reference into this specification.

One may utilize conventional sputtering devices in this process. By way of illustration and not limitation, a typical sputtering system is described in U.S. Pat. No. 5,178,739, the entire disclosure of which is hereby incorporated by reference into this specification. As is disclosed in this patent, " . . . a sputter system 10 includes a vacuum chamber 20, which contains a circular end sputter target 12, a hollow, cylindrical, thin, cathode magnetron target 14, a RF coil 16 and a chuck 18, which holds a semiconductor substrate 19. The atmosphere inside the vacuum chamber 20 is controlled through channel 22 by a pump (not shown). The vacuum chamber 20 is cylindrical and has a series of permanent magnets 24 positioned around the chamber and in close proximity therewith to create a multiple field configuration near the interior surface 15 of target 12. Magnets 26, 28 are placed above end sputter target 12 to also create a multipole field in proximity to target 12. A singular magnet 26 is placed above the center of target 12 with a plurality of other magnets 28 disposed in a circular formation around magnet 26. For convenience, only two magnets 24 and 28 are shown. The configuration of target 12 with magnets 26, 28 comprises a magnetron sputter source 29 known in the prior art, such as the Torus-10E system manufactured by K. Lesker, Inc. A sputter power supply 30 (DC or RF) is connected by a line 32 to the sputter target 12. A RF supply 34 provides power to RF coil 16 by a line 36 and through a matching network 37. Variable impedance 38 is connected in series with the cold end 17 of coil 16. A second sputter power supply 39 is connected by a line 40 to cylindrical sputter target 14. A bias power supply 42 (DC or RF) is connected by a line 44 to chuck 18 in order to provide electrical bias to substrate 19 placed thereon, in a manner well known in the prior art."

By way of yet further illustration, other conventional sputtering systems and processes are described in U.S. Pat. No. 5,569,506 (a modified Kurt Lesker sputtering system), U.S. Pat. No. 5,824,761 (a Lesker Torus 10 sputter cathode), U.S. Pat. Nos. 5,768,123, 5,645,910, 6,046,398 (sputter deposition with a Kurt J. Lesker Co. Torus 2 sputter gun), U.S. Pat. Nos. 5,736,488, 5,567,673, 6,454,910, and the like. The entire disclosure of each of these United States patents is hereby incorporated by reference into this specification.

By way of yet further illustration, one may use the techniques described in a paper by Xingwu Wang et al. entitled "Technique Devised for Sputtering AlN Thin Films," published in "the Glass Researcher," Volume 11, No. 2 (Dec. 12, 2002). The entire disclosure of this publication is hereby incorporated by reference into this specification.

In one preferred embodiment, a magnetron sputtering technique is utilized, with a Lesker Super System III system. The vacuum chamber of this system is cylindrical, with a diameter of approximately one meter and a height of approximately 0.6 meters. The base pressure used is from about 0.001 to 0.0001 Pascals. In one aspect of this process, the target is a metallic FeAl disk, with a diameter of approximately 0.1 meter. The molar ratio between iron and aluminum used in this aspect is approximately 70/30. Thus, the starting composition in this aspect is almost non-magnetic. See, e.g., page 83 (FIG. 3.1$aii$) of R. S. Tebble et al.'s "Magnetic Materials" (Wiley-Interscience, New York, N.Y., 1969); this Figure discloses that a bulk composition containing iron and aluminum with at least 30 mole percent of aluminum (by total moles of iron and aluminum) is substantially non-magnetic.

In this aspect, to fabricate FeAl films, a DC power source is utilized, with a power level of from about 150 to about 550 watts (Advanced Energy Company of Colorado, model MDX Magnetron Drive). The sputtering gas used in this aspect is argon, with a flow rate of from about 0.0012 to about 0.0018 standard cubic meters per second. To fabricate FeAlN films in this aspect, in addition to the DC source, a pulse-forming device is utilized, with a frequency of from about 50 to about 250 MHz (Advanced Energy Company, model Sparc-le V). One may fabricate FeAlO films in a similar manner but using oxygen rather than nitrogen.

In this aspect, a typical argon flow rate is from about (0.9 to about 1.5)$\times 10^{-3}$ standard cubic meters per second; a typical nitrogen flow rate is from about (0.9 to about 1.8)$\times 10^{-3}$ standard cubic meters per second; and a typical oxygen flow rate is from about (0.5 to about 2)$\times 10^{-3}$ standard cubic meters per second. During fabrication, the pressure typically is maintained at from about 0.2 to about 0.4 Pascals. Such a pressure range is found to be suitable for nanomagnetic materials fabrications.

In this aspect, the substrate used may be either flat or curved. A typical flat substrate is a silicon wafer with or without a thermally grown silicon dioxide layer, and its diameter is preferably from about 0.1 to about 0.15 meters. A typical curved substrate is an aluminum rod or a stainless steel wire, with a length of from about 0.10 to about 0.56 meters and a diameter of from (about 0.8 to about 3.0)$\times 10^{-3}$ meters The distance between the substrate and the target is preferably from about 0.05 to about 0.26 meters.

In this aspect, in order to deposit a film on a wafer, the wafer is fixed on a substrate holder. The substrate may or may not be rotated during deposition. In one embodiment, to deposit a film on a rod or wire, the rod or wire is rotated at a rotational speed of from about 0.01 to about 0.1 revolutions per second, and it is moved slowly back and forth along its symmetrical axis with a maximum speed of about 0.01 meters per second.

In this aspect, to achieve a film deposition rate on the flat wafer of $5 \times 10^{-10}$ meters per second, the power required for the FeAl film is 200 watts, and the power required for the FeAlN film is 500 watts The resistivity of the FeAlN film is approximately one order of magnitude larger than that of the metallic FeAl film. Similarly, the resistivity of the FeAlO filmis about one order of magnitude larger than that of the metallic FeAl film.

Iron containing magnetic materials, such as FeAl, FeAlN and FeAlO, have been fabricated by various techniques. The magnetic properties of those materials vary with stoichiometric ratios, particle sizes, and fabrication conditions; see, e.g., R. S. Tebble and D. J. Craik, "Magnetic Materials", pp. 81–88, Wiley-Interscience, New York, 1969. As is disclosed in this reference, when the iron molar ratio in bulk FeAl materials is less than 70 percent or so, the materials will no longer exhibit magnetic properties.

However, it has been discovered that, in contrast to bulk materials, a thin film material often exhibits different properties due to the constraint provided by the substrate.

Nanomagnetic Compositions Comprised of Moieties A, B, and C

Figure 2:
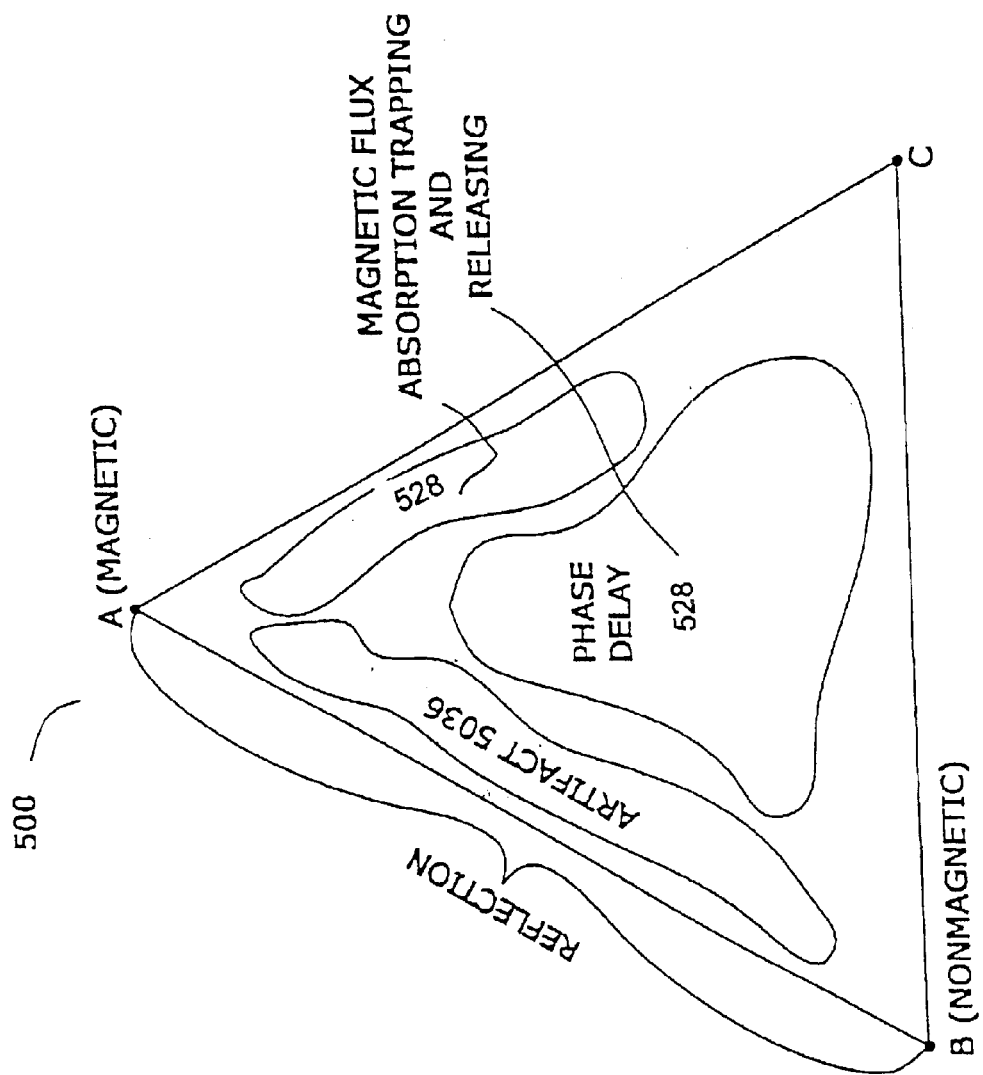
FIG. 2 is a phase diagram illustrating certain preferred compositions useful in the process of this invention.

The aforementioned process may be adapted to produce other, comparable thin films, as is illustrated in FIG. 2.

Referring to FIG. 2, and in the preferred embodiment depicted therein, a phase diagram 500 is presented. As is illustrated by this phase diagram 500, the nanomagnetic material used in the composition of this invention preferably is comprised of one or more of moieties A, B, and C.

The moiety A depicted in phase diagram 500 is a magnetic element selected from the group consisting of a transition series metal, a rare earth series metal, or actinide metal, a mixture thereof, and/or an alloy thereof.

As is known to those skilled in the art, the transition series metals include chromium, manganese, iron, cobalt, nickel. One may use alloys or iron, cobalt and nickel such as, e.g., iron-aluminum, iron-carbon, iron-chromium, iron-cobalt, iron-nickel, iron nitride ($Fe^3N$), iron phosphide, iron-silicon, iron-vanadium, nickel-cobalt, nickel-copper, and the like. One may use alloys of manganese such as, e.g., manganese-aluminum, manganese-bismuth, MnAs, MnSb, MnTe, manganese-copper, manganese-gold, manganese-nickel, manganese-sulfur and related compounds, manganese-antimony, manganese-tin, manganese-zinc, Heusler alloy, and the like. One may use compounds and alloys of the iron group, including oxides of the iron group, halides of the iron group, borides of the transition elements, sulfides of the iron group, platinum and palladium with the iron group, chromium compounds, and the like.

One may use a rare earth and/or actinide metal such as, e.g., Ce, Pr, Nd, Pm, Sm, Eu, Gd, Tb, Dy, Ho, Er, Tm, Yb, Lu, La, mixtures thereof, and alloys thereof. One may also use one or more of the actinides such as, e.g., Th, Pa, U, Np, Pu, Am, Cm, Bk, Cf, Es, Fm, Md, No, Lr, Ac, and the like.

These moieties, compounds thereof, and alloys thereof are well known and are described, e.g., in the aforementioned text of R. S. Tebble et al. entitled "Magnetic materials."

In one preferred embodiment, moiety A is selected from the group consisting of iron, nickel, cobalt, alloys thereof, and mixtures thereof. In this embodiment, the element A is magnetic, i.e., it has a relative magnetic permeability of from about 1 to about 500,000. As is known to those skilled in the art, relative magnetic permeability is a factor, characteristic of a material, that is proportional to the magnetic induction produced in a material divided by the magnetic field strength; it is a tensor when these quantities are not parallel. See, e.g., page 4–128 of E. U. Condon et al.'s "Handbook of Physics" (McGraw-Hill Book Company, Inc., New York, N.Y., 1958).

The moiety A also preferably has a saturation magnetization of from about 1 to about 36,000 Gauss, and a coercive force of from about 0.01 to about 5,000 Oersteds.

The moiety A may be present in the nanomagnelic material either in its elemental form, as an alloy, in a solid solution, or as a compound.

It is preferred at least about 1 mole percent of moiety A be present in the nanomagnetic material (by total moles of A, B, and C), and it is more preferred that at least 10 mole percent of such moiety A be present in the nanomagnetic material (by total moles of A, B, and C). In one embodiment, at least 60 mole percent of such moiety A is present in the nanomagnetic material, (by total moles of A, B, and C.)

In addition to moiety A, it is preferred to have moiety B be present in the nanomagnetic material. In this embodiment, moieties A and B are admixed with each other. The mixture may be a physical mixture, it may be a solid solution, they may be alloyed, etc.

In one embodiment, the magnetic material A is dispersed within nonmagnetic material B. In this embodiment, the nanomagnetic material may be comprised of 100 percent of moiety A. Alternatively, the nanomagnetic material may be comprised of both moiety A and moiety B.

When moiety B is present in the nanomagnetic material, in whatever form or forms it is present, it is preferred that it be present at a mole ratio (by total moles of A and B) of from about 1 to about 99 percent and, preferably, from about 10 to about 90 percent.

The B moiety, in whatever form it is present, is nonmagnetic, i.e., it has a relative magnetic permeability of 1.0; without wishing to be bound to any particular theory, applicants believe that the B moiety acts as buffer between adjacent A moieties. One may use, e.g., such elements as silicon, aluminum, boron, platinum, tantalum, palladium, yttrium, zirconium, titanium, calcium, beryllium, barium, silver, gold, indium, lead, tin, antimony, germanium, gallium, tungsten, bismuth, strontium, magnesium, zinc, and the like.

In one embodiment, and without wishing to be bound to any particular theory, it is believed that B moiety provides plasticity to the nanomagnetic material that it would not have but for the presence of B. It is preferred that the bending radius of a substrate coated with both A and B moieties be at least 110 percent as great as the bending radius of a substrate coated with only the A moiety.

The use of the B material allows one to produce a coated substrate with a springback angle of less than about 45 degrees. As is known to those skilled in the art, all materials have a finite modulus of elasticity; thus, plastic deformationis followed by some elastic recovery when the load is removed. In bending, this recovery is called springback. See, e.g., page 462 of S. Kalparjian's "Manufacturing Engineering and Technology," Third Edition (Addison Wesley Publishing Company, New York, N.Y., 1995).

Referring again to FIG. 2, when an electromagnetic field is incident upon the nanomagnetic material comprised of A and B, such field will be reflected to some degree depending upon the ratio of moiety A and moiety B.

Referring again to FIG. 2, and in one embodiment, the nanomagnetic material is comprised of moiety A, moiety C, and optionally moiety B. The moiety C is preferably selected from the group consisting of elemental oxygen, elemental nitrogen, elemental carbon, elemental fluorine, elemental chlorine, elemental hydrogen, and elemental helium, elemental neon, elemental argon, elemental krypton, elemental xenon, and the like.

It is preferred, when the C moiety is present, that it be present in a concentration of from about 1 to about 90 mole percent, based upon the total number of moles of the A moiety and/or the B moiety and C moiety in the composition.

Referring again to FIG. 2, and in the embodiment depicted, the area 528 produces a composition which optimizes the degree to which magnetic flux are initially trapped and/or thereafter released by the composition when a magnetic field is withdrawing from the composition.

Without wishing to be bound to any particular theory, applicants believe that, when a composition as described by area 528 is subjected to an alternating magnetic field, at least a portion of the magnetic field is trapped by the composition when the field is strong, and then this portion tends to be released when the field releases and lessens in intensity.

The molar ratio of A/(A and B and C) generally is from about 1 to about 99 mole percent and, preferably, from about 10 to about 90 molar percent. In one embodiment, such molar ratio is from about 30 to about 60 molar percent.

The molar ratio of B/(A plus B plus C) generally is from about 1 to about 99 mole percent and, preferably, from about 10 to about 40 mole percent.

The molar ratio of C/(A plus B plus C) generally is from about 1 to about 99 mole percent and, preferably, from about 10 to about 50 mole percent.

A Magnetic Shield with a Squareness Ratio of from about 0.5 to About 1.0

In one preferred embodiment of this invention, the nanomagnetic film 104 (see FIG. 1) has a squareness of from about 0.5 to about 1.0 and, more preferably, from about 0.8 to about 1.0. The term squareness, as used in this specification, is the ratio of the remanent magnetization (Mr) to the saturization magnetization (Ms).

Page 4–128 of E. U Condon et al.'s "Handbook of Physics" (McGraw-Hill Book Company, Inc., New York, N.Y., 1958) presents "FIG. 8.2" that describes "Important constants of the technical magnetization curve;" a graph is presented in which the magnetic moment of the film (in electromagnetic units is plotted against the field (in Oersteds). These constants include " . . . $u_o$ and $x_o$, initial permeability and susceptibility; $u_{max}$ (maximum permeability); $B_r$ and $M_r$ (remanent flux density (=induction) and magnetization . . . ."

It will be apparent from this FIG. 8.2, and the prior art, the ratio of $M_r$ to $M_s$ is the "squareness." Ideally, this ratio is as high as possible, ideally equaling 1.0.

For other discussions of the ratio of $M_r$ to $M_s$ reference also may be had to, e.g., U.S. Pat. No. 4,652,499 (sec lines 10–13 of column 3), U.S. Pat Nos. 6,456,448, 6,395,413, 6,372,338, 6,183,606, 6,146,776, 6,118,624, 6,004,654, 5,789,069, 5,783,284, 5,736,236, 5,514,452, 5,510,172, 5,244,751, 5,180,640, 5,068,144, 4,798,765, 4,731,300, 4,232,071, 6,500,567, 6,150,015, and the like. The entire disclosure of each of these United States patents is hereby incorporated by reference into this specification.

In one preferred embodiment of this invention, the non-magnetic film of this invention has a magnetic anisotropy of less than about 20 degrees and, preferably, less than about 15 degrees.

As is known to those skilled the art, "One factor which may strongly affect the shape of the M,H (or B,H) curve, or the shape of the hysteresis loop, is magnetic anisotropy. This term simply means that the magnetic properties depend on the direction in which they are measured." See page 207 of B. D. Cullity's "Introduction to Magnetic Materials" (Addison-Wesley Publishing Company, Reading, Mass., 1972).

The magnetic anisotropy of a film may be measured by conventional means. Thus, e.g., one may measure the magnetic anisotropy by a torque magetometer. Reference may be had, e.g., to U.S. Pat. No. 5,798,641 (torque magnetometer using integrated piezoelectric levers), U.S. Pat. No. 5,739,686 (electrically insulating cantilever magnetometer with mutually isolated and integrated thermometry), U.S. Pat. No. 4,939,045 (magnetic recording medium), U.S. Pat. No. 3,609,526 (contactless method and apparatus for determining electrical resistivity), and the like. The entire disclosure of each of these United States patents is hereby incorporated by reference into this specification.

By way of further illustration, reference may be had to Ronald F. Soohoo's "Magnetic Thin Films" (Harper & Row, New York, N.Y., 1965). As is disclosed on pages 128–129 of this reference, magnetic anisotropy may be measured by the Hysteresis-Looper Method in accordance with the equation: M sin(theta)=M $(H_t/2K_t/M)$, wherein theta is the angle between the magnetziation and the easy axis at a given transverse field $H_t$. As is disclosed in this test, "It is seen from the equation that the transverse loop is a straight line without hysteresis and saturates at $H_t=2K_t/M$. Thus, the transverse loop can be used to determine both M and the anisotropy field $H_k=2K_t/M$. In practice, however, the closed loop exists only at $H_t<2K_t/M$. At high drives, the loop opens up and encloses a finite area as shown by the dotted curve in FIG. 8.5. Therefore, $H_k$ is usually determined by the hysteresis loper method in the following way. The easy-axis rectangular hysteresis loop is first displayed on the face of the oscilloscope and the saturation level of the loop is noted. Next, the low level transverse loop is displayed. If the straight line so exhibited is extended until it intersects with the horizontal saturation line determined by the easy-axis loop, $H_k$ may be determined. The procedure is illustrated in FIG. 7.9."

By way of further illustration, one may use a magnetic inspection probe for measurement of magnetic anisotropy. Such a probe is disclosed, e.g., in U.S. Pat. No. 5,475,305, which describes and claims: "a magnetic inspection probe for measuring the magnetic properties of an anisotropic test specimen by making magnetic measurements in at least two directions oriented in a known manner to one another across the surface of the test specimen without the need to reorient the probe, the inspection probe comprising: the probe having a body and core of respectively different shapes oriented to create a two-dimensional multi-directional magnetic field therebetween for introducing the magnetic field into the test specimen; means for measuring the magnetic flux within the test specimen resulting from the introduction of the magnetic field; and at least two sensor means in the probe oriented in different directions with respect to each other for measuring simultaneously in two or more directions of the two-dimensional magnetic field, without reorientation of the probe, the magnetic field intensity adjacent to the surface of the test specimen caused by the introduction of the magnetic field into the specimen."

In one preferred embodiment, the film containing nanon-magnetic material has a stress of less about 500 megaPascals and, more preferably, less than about 100 megaPascals. One may measure the stress of a film deposited onto a substrate by conventional means. Reference may be had, e.g., U.S. Pat. No. 5,864,393 (optical method for the determination of stress in thin films), U.S. Pat. No. 6,208,418 (apparatus for measurement of the mechanical properties of thin films), U.S. Pat. Nos. 6,205,918, 5,310,263, 4,878,085, 4,314,894, 4,274,935, 6,417,483, and the like. The entire disclosure of each of these United States patents is hereby incorporated by reference into this specification.

In one preferred embodiment, the film containing nano-magnetic material has a surface roughness of less than 4 nanometers. In one embodiment, the film has a surface roughness of less than 3 nanometers. In another embodiment, the film has a surface roughness of less than 2 nanometers. One may measure surface roughness by conventional means. Reference may be had, e.g., to U.S. Pat. No. 4,145,140 (measurement of surface roughness), U.S. Pat. Nos. 6,120,877, 5,729,374, 5,608,527 (apparatus and method for dynamic measurement of surface roughness), U.S. Pat. Nos. 4,976,545, 4,878,114 (method an apparatus for assessing surface roughness), U.S. Pat. Nos. 4,080,741, 3,971,956 (measurement of surface roughness), and the like. The entire disclosure of each of these United States patents is hereby incorporated by reference into this specification.

In one embodiment of the process of this invention, the stress of the as-deposited film is controlled by controlling the deposition pressure of the gases used in the sputtering deposition chamber. In this embodiment, the pressure of such gas should preferably range from about 1 milliTorr to about 5 milliTorr.

The following examples are presented to illustrate the invention but are not to be deemed limitative thereof. Unless otherwise specified, all parts are by weight and temperatures are in degrees Centigrade.

EXAMPLE 1

Preparation of an Insulating Film

In the experiment of this Example, a metallic target consisting of Aluminum-Iron, in the presence of Nitrogen, was utilized to fabricate an Aluminum Iron Nitride film. An attempt was made to fully nitride the AlFe target in order to deposit AlFeN; and an attempt was also made to keep the insulating layer very thin to prevent arcing within the chamber. A pulsed DC power supply was utilized for this purpose. This supply had an internal wave generator to provide a low frequency (30–300 kHz) square wave, with an adjustable positive pulse width. This feature returned the target to metallic prior to each negative cycle—thus allowing a robust process window. To maintain stability during this process, the target crossover point was defined.

There were many variables to consider when determining the proper process window for stoichometric material. These included, but are not limited to: Argon flow, Nitrogen flow, chamber pressure, vacuum pumping speed, also power supply power, frequency, pulse width, and positive pulse amplitude.

The crossover point is defined as that point where the target is nitrided during the entire negative going pulse, and changed to metallic just prior to the pulse going negative. This will change for any given parameter change, thus requiring determination of that crossover point any time a change is made. To determine the crossover point, all variables must be set, and must remain a constant. Next, Nitrogen flow is varied in I sccm increments, and pressure, voltage and current are recorded. Note: the pumping speed must remain constant, i.e. the system must not regulate pumping speed to maintain constant pressure.

In the experiment of this Example, the Argon flow was set to 20 sccm, and the pumping speed was set to 2.0 mTorr. The power supply was regulated to power, and set to 500 watts. Additionally, the pulse frequency was set to 100 kHz, and the positive pulse width to 2 microseconds (20%). Nitrogen was introduced, and increased in 1 sccm steps, while the voltage, current, and chamber pressure were recorded.

At measurements points 1–30, the nitrogen flow, the pressure, the measured voltage, and the measured amperage (whose units were millTorrs, volts, and amperes, respectively) were, respectively:1: 2.07, 295, 1.76; 2: 2.11, 298, 1.74; 3: 2.16, 300, 1.72; 4: 2.21, 300, 1.72; 5: 2.26, 300, 1.72; 6: 2.33, 299, 1.74; 7:240, 298, 1.74; 8: 2.46, 296, 1.76; 9: 2.54,294, 1.76; 10: 2.61, 292, 1.78; 11: 2.68,290, 1.78; 12: 2.75, 288, 1.80; 13: 2.83,286, 1.82; 14: 2.90, 284, 1.82; 15: 2.98, 282, 1.84; 16: 3.05,280, 1.86; 17: 3.13,278, 1.88; 18: 3.20, 274, 1.92; 19: 3.27, 271, 1.92; 20: 3.36, 268, 1.94; 21: 3.42, 268, 1.94; 22: 3.50, 268, 1.94; 23: 3.56, 268, 1.94; 24: 3.64, 268, 1.94; 25: 3.71, 268, 1.94; 26: 3.77, 268, 1.94; 27: 3.84, 268, 1.94; 28: 3.89, 268, 1.94; 29: 3.96, 268, 1.94; and 30: 4.03, 268, 1.94.

As can be seen from this data, The cross-over point was not necessarily obvious; however, it was present at 20 s.c.c.m. of nitrogen. Depositing a film with the previously mentioned parameters held constant; and, at 23 sccm of nitrogen, resulted in a film with a resistivity one order of magnitude higher than its metallic counterpart.

EXAMPLE 2

Film Stress Variation

In the experiments of this Example, stress-free film deposition was attempted. Stress free film deposition is essential if the device requires multiple levels of films, or they are to be ductile. Stress free is defined as <100 MPa compressive or tensile, while low stress is <500 MPa compressive or <250 MPa tensile. When utilizing fixed magnet magnetrons (as opposed to rotating magnet magnetrons), the chamber pressure is the primary parameter varied to determine stress.

In one experiment, films were first deposited onto two samples (ALF03 and 5W2062) at the parameters indicated at 23 sccm Nitrogen (3.2 mTorr) in the crossover curve produced by the data of EXAMPLE 1. The first sample was 4137 Angstroms of AlFeN deposited onto a 6" Silicon wafer. The second sample was 11,120 Angstroms of AlFeN deposited onto a 6" Silicon wafer. The measured stress at these deposition conditions was measured on a Flexus 2010 tool as 640 MPa and 674 MPa Compressive, respectively.

An AlFeN film was deposited onto a 6" Silicon wafer (5W2058). At 23 sccm nitrogen, the pumping speed was decreased such that the chamber pressure was 4.36 mTorr during deposition. This film was 9010 Angstroms thick and exhibited a stress of 463 MPa Compressive.

It was discovered that depositing a film at higher pressures will yield even lower stress values. The crossover curve had to be regenerated in each instance

EXAMPLE 3

Film Surface Roughness

The surface roughness of any item contacting the internal organs of a human being is significant; for a very rough surface could potentially tear body tissue. I the experiment of this example, the surface roughness of the film of a wafer "5W2058" (whose deposition conditions are described in the experiment of Example 2) was measured on an Atomic Force Microscope (AFM). These measurements indicated an RMS deviation of 45.21 Angstroms. By way of comparison, the surface roughness of a nylon tube typically used is the human body is often on the order of about 100 Angstroms.

While the invention has been described with reference to preferred embodiments, it is to be understood that variations and modifications may be resorted to as will be apparent to those skilled in the art. Such variations and modifications are to be considered within the purview and scope of the invention as defined by the claims appended hereto.

We claim:

1. A magnetically shielded substrate assembly comprised of a substrate and, disposed over such substrate, a magnetic shield, wherein:
   (a) said magnetic shield, when exposed to a magnetic field with an intensity of at least 0.5 Teslas, has a magnetic shielding factor of at least about 0.5;
   (b) said magnetic shield is comprised of a film of nanomagnetic material comprising at least about 40 weight percent of nanomagnetic material with a mass density of at least about 0.01 grams per cubic centimeter, a saturation magnetization of from about 1 to about 36,000 Gauss, a coercive force of from about 0.01 to about 5,000 Oersteds, a relative magnetic permeability of from about 1 to about 500,000, and an average particle size of less than about 100 nanometers; and
   (c) said film of nanomagnetic material has a squareness of from about 0.5 to about 1.0.

2. A magnetically shielded substrate assembly comprised of a substrate and, disposed over such substrate, a magnetic shield, wherein:
   (a) said magnetic shield, when exposed to a magnetic field with an intensity of at least 0.5 Teslas, has a magnetic shielding factor of at least about 0.5;
   (b) said magnetic shield is comprised of a film of nanomagnetic material comprising at least about 40 weight percent of nanomagnetic material with a mass density of at least about 0.01 grams per cubic centimeter, a saturation magnetization of from about 1 to about 36,000 Gauss, a coercive force of from about 0.01 to about 5,000 Oersteds, a relative magnetic permeability of from about 1 to about 500,000, and an average particle size of less than about 100 nanometers; and
   (c) said film of nanomagnetic material has a stress of less than about 500 megaPascals.

3. A magnetically shielded substrate assembly comprised of a substrate and, disposed over such substrate, a magnetic shield, wherein:
   (a) said magnetic shield, when exposed to a magnetic field with an intensity of at least 0.5 Teslas, has a magnetic shielding factor of at least about 0.5;
   (b) said magnetic shield is comprised of a film of nanomagnetic material comprising at least about 40 weight percent of nanomagnetic material with a mass density of at least about 0.01 grams per cubic centimeter, a saturation magnetization of from about 1 to about 36,000 Gauss, a coercive force of from about 0.01 to about 5,000 Oersteds, a relative magnetic permeability of from about 1 to about 500,000, and an average particle size of less than about 100 nanometers; and
   (c) said film of nanomagnetic material has a magnetic anisotropy of less than about 20 degrees.

4. The magnetically shielded substrate assembly as recited in claim 1, wherein said film of nanomagnetic material has a magnetic anisotropy of less than about 20 degrees.

5. The magnetically shielded substrate assembly as recited in claim 4, wherein said film of nanomagnetic material has a stress of less than about 500 megapascals.

6. The magnetically shielded substrate assembly as recited in claim 5, wherein said film of nanomagnetic material has a surface roughness of less than 4 nanometers.

7. The magnetically shielded substrate assembly as recited in claim 5, wherein said film of nanomagnetic material has a thickness of less than about 2 microns.

8. The magnetically shielded substrate assembly as recited in claim 5, wherein said magnetically shielded conductor assembly has a bend radius of less than 2 centimeters.

9. The magnetically shielded substrate assembly as recited in claim 5, wherein said film of nanomagnetic material has a magnetic shielding factor of at least about 0.9.

10. The magnetically shielded substrate assembly as recited in claim 5, wherein said nanomagnetic material has a coercive force of from about 0.1 to about 10 Oersteds.

11. The magnetically shielded substrate assembly as recited in claim 5, wherein said nanomagnetic material has a relative magnetic permeability of from about 1.5 to about 260,000.

12. The magnetically shielded substrate assembly as recited in claim 5, wherein said nanomagnetic material has a mass density of at least about 1 gram per cubic centimeter.

13. The magnetically shielded substrate assembly as recited in claim 12, wherein said nanomagnetic material has a mass density of at least 3 grams per cubic centimeter.

14. The magnetically shielded substrate assembly as recited in claim 5, wherein said nanomagnetic material is comprised of particles with a particle size of from about 2 to about 50 nanometers.

15. The magnetically shielded substrate assembly as recited in claim 5, wherein said film of nanomagnetic material has a thickness of from about 0.1 to about 3 microns.

16. The magnetically shielded substrate assembly as recited in claim 5, wherein said film of nanomagnetic material has a saturation magnetization of from about 500 to about 10,000 Gauss.

17. The magnetically shielded substrate assembly as recited in claim 5, wherein said film of nanomagnetic material has a saturation magnetization in excess of 20,000 Gauss.

18. The magnetically shielded substrate assembly as recited in claim 5, wherein said nanomagnetic material is disposed within an insulating matrix.

* * * * *